US009239301B2

(12) United States Patent
Kikuchi et al.

(10) Patent No.: US 9,239,301 B2
(45) Date of Patent: Jan. 19, 2016

(54) IMAGE PROCESSING APPARATUS, IMAGE PROCESSING METHOD, AND IMAGE PROCESSING SYSTEM

(71) Applicant: Sony Corporation, Tokyo (JP)

(72) Inventors: Daisuke Kikuchi, Kanagawa (JP); Hiromi Yoshinari, Kanagawa (JP); Hisakazu Shiraki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 200 days.

(21) Appl. No.: 13/968,469

(22) Filed: Aug. 16, 2013

(65) Prior Publication Data

US 2014/0056402 A1    Feb. 27, 2014

(30) Foreign Application Priority Data

Aug. 24, 2012 (JP) ................... 2012-185292

(51) Int. Cl.
*G01N 23/04* (2006.01)
*G06T 11/00* (2006.01)
*A61B 6/03* (2006.01)

(52) U.S. Cl.
CPC ............ *G01N 23/046* (2013.01); *G06T 11/006* (2013.01); *A61B 6/032* (2013.01); *G06T 2211/424* (2013.01)

(58) Field of Classification Search
CPC ........ A61B 6/025; A61B 6/032; A61B 6/405; A61B 6/4064; A61B 6/027; A61B 6/4085; G01N 23/046; G01N 2223/419; G06T 11/006; G06T 2211/424
USPC ................... 378/4, 19, 21, 145, 901
See application file for complete search history.

(56) References Cited

U.S. PATENT DOCUMENTS

2005/0105678 A1*  5/2005  Nakashima ............ 378/4
2008/0170653 A1*  7/2008  Ando et al. ............ 378/6

* cited by examiner

*Primary Examiner* — Irakli Kiknadze
*Assistant Examiner* — Julio M Duarte-Carvajalino
(74) *Attorney, Agent, or Firm* — Hazuki International, LLC

(57) ABSTRACT

There is provided an image processing apparatus including a processing unit configured to processes projection data in which X-ray detection data representing a detection result of parallel beam X-rays output from an X-ray source has been converted by projection, and form an X-ray image based on the X-ray detection data.

8 Claims, 10 Drawing Sheets

IMAGE PROCESSING APPARATUS, IMAGE PROCESSING METHOD, AND IMAGE PROCESSING SYSTEM

BACKGROUND

The present disclosure relates to an image processing apparatus, an image processing method, and an image processing system.

For example, a CT (computed tomography) apparatus (or a CT system; hereinafter, the same) that utilizes X-rays output from an X-ray source or an apparatus (or a system; hereinafter, the same) having a tomosynthesis function that utilizes X-rays is widely used in the medical field, for example. JP-A-2004-329784 describes a technology relating to a CT apparatus that utilizes X-rays.

SUMMARY

A CT apparatus and the like that utilizes X-rays forms an X-ray image by processing X-ray detection data representing a detection result of X-rays. More specifically, in a CT apparatus and the like that utilizes X-rays, an X-ray image is formed based on X-ray detection data being converted into projection data, and three-dimensional data being reconstituted from the projection data, for example.

Here, in a CT apparatus and the like that utilizes X-rays, an X-ray source that outputs cone beam X-rays is used, or an X-ray source that outputs fan beam X-rays like the technology described in JP-A-2004-329784 is used, for example.

However, when forming an X-ray image by processing projection data in which X-ray detection data representing a result that X-rays output from an X-ray source that outputs cone beam X-rays or an X-ray source that outputs fan beam X-rays have been detected has been converted, mixing of data of a plurality of layers of a target that is hit by the X-rays occurs in the projection data due to widening and unevenness of the detection intensity resulting from the cone beam or the fan beam, for example. Further, in order to strictly carry out the reconstitution of three-dimensional data from projection data in which data from various layers is mixed like this, calculations are performed that repeatedly use all of the projection data and all of the reconstitution data.

Therefore, to form an X-ray image having greater accuracy by processing projection data in which X-ray detection data representing a result that X-rays output from an X-ray source that outputs cone beam X-rays or an X-ray source that outputs fan beam X-rays have been detected has been converted, the calculation costs for forming the X-ray image become very large.

Examples of methods for performing the calculations for forming an X-ray image more rapidly include ignoring the effects caused by a cone beam or a fan beam, or converting a cone beam or a fan beam into a parallel beam in the projection data and dividing the processing for forming the X-ray image.

However, when using such a method for performing the calculations for forming an X-ray image more rapidly, since approximate processing is included when forming the X-ray image, the calculation accuracy deteriorates, so that the accuracy of the obtained X-ray image deteriorates.

According to an embodiment of the present disclosure, there are provided a novel and improved image processing apparatus, image processing method, and image processing system that can achieve a higher quality X-ray image while reducing the calculation costs for reconstituting an X-ray image even further.

According to an embodiment of the present disclosure, there is provided an image processing apparatus including a processing unit configured to processes projection data in which X-ray detection data representing a detection result of parallel beam X-rays output from an X-ray source has been converted by projection, and form an X-ray image based on the X-ray detection data.

Further, according to an embodiment of the present disclosure, there is provided an image processing method including processing projection data in which X-ray detection data representing a detection result of parallel beam X-rays output from an X-ray source has been converted by projection, and forming an X-ray image based on the X-ray detection data.

Further, according to an embodiment of the present disclosure, there is provided an image processing system including an X-ray output apparatus that includes an X-ray source for outputting parallel beam X-rays, a detection apparatus configured to detect the parallel beam X-rays, generate X-ray detection data representing a detection result of the parallel beam X-rays, and convert the generated X-ray detection data into projection data by projection, and an image processing apparatus that includes a processing unit configured to process projection data in which the X-ray detection data has been converted, and form an X-ray image based on the X-ray detection data.

According to the embodiments of the present disclosure described above, a higher quality X-ray image can be achieved while reducing the calculation costs for reconstituting an X-ray image even further.

DETAILED DESCRIPTION OF THE EMBODIMENT(S)

Figure 1:
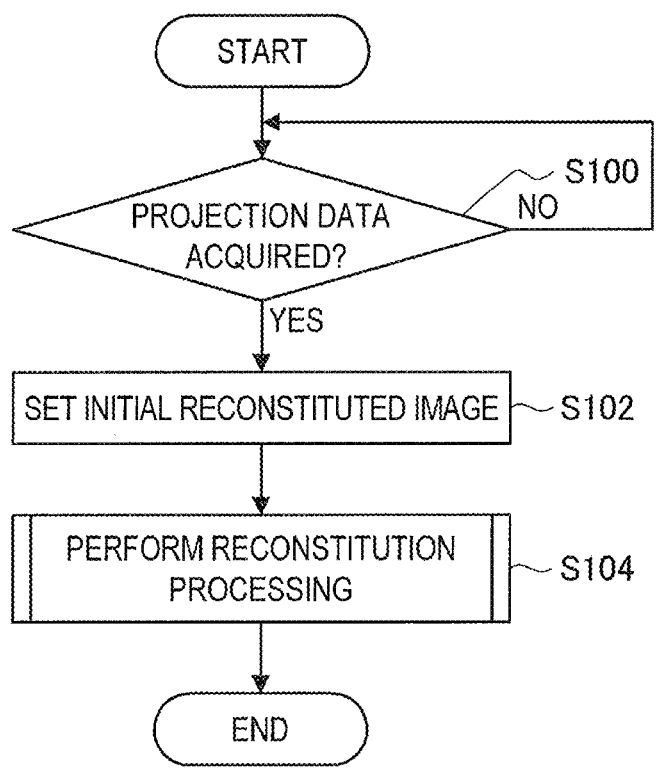
FIG. 1 is a flow diagram illustrating a first example of the processing performed in an image processing method according to an embodiment of the present disclosure performed by an image processing apparatus according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, the description will be made in the following order.
1. Image processing method according to the present embodiment
2. Image processing apparatus according to the present embodiment
3. Program according to the present embodiment
(Image Processing Method According to the Present Embodiment)

Before describing the configuration of the image processing apparatus according to the present embodiment, first, the image processing method according to the present embodiment will be described. In the following, the image processing method according to the present embodiment will be described based on an example in which the image processing apparatus according to the present embodiment performs the processing performed in the image processing method according to the present embodiment.

(1) Outline of the Image Processing Method According to the Present Embodiment

As described above, when forming an X-ray image having greater accuracy by processing projection data in which X-ray detection data representing a result that X-rays output from an X-ray source that outputs cone beam X-rays or an X-ray source that outputs fan beam X-rays have been detected has been converted, the calculation costs for forming the X-ray image become very large. Further, when using the above-described method for performing the calculations for forming an X-ray image more rapidly, since approximate processing is included when forming the X-ray image, the calculation accuracy deteriorates, so that the accuracy of the obtained X-ray image deteriorates.

Accordingly, the image processing apparatus according to the present embodiment forms an X-ray image based on X-ray detection data by processing projection data in which X-ray detection data representing a detection result of parallel beam X-rays output from an X-ray source has been converted.

Here, the X-ray detection data according to the present embodiment is, for example, data representing a detection intensity of parallel beam X-rays that have passed through a target and have been detected by a detector, such as the detector that is included in the below-described detection apparatus according to the present embodiment. In the following, to differentiate between the X-ray detection data according to the present embodiment and the X-ray detection data representing a detection result of cone beam X-rays or fan beam X-rays, the X-ray detection data according to the present embodiment is sometimes referred to as "parallel X-ray detection data".

The parallel X-ray detection data representing the detection intensity of the parallel beam X-rays detected by the above-described detector is converted into projection data (two-dimensional projection data) by being projected in two dimensions as an X-ray projection image. More specifically, the parallel X-ray detection data is converted into projection data by radon conversion, for example.

Here, although the conversion processing for converting the parallel X-ray detection data into projection data is performed by an external device, such as the detection apparatus (described below) according to the present embodiment, that generates the X-ray detection data according to the present embodiment, for example, the conversion processing according to the present embodiment is not limited to being performed by an external device. For example, the image processing apparatus according to the present embodiment may perform the conversion processing according to the present embodiment. In the following, the processing performed in the image processing method according to the present embodiment will be described mainly based on an example in which the conversion processing according to the present embodiment is performed by an external device, such as the detection apparatus according to the present embodiment, that generates parallel X-ray detection data, namely, a case in which the image processing apparatus according to the present embodiment processes projection data in which the parallel X-ray detection data has already been converted by the external device.

Further, although the image processing apparatus according to the present embodiment processes projection data in which parallel X-ray detection data has been converted, or parallel X-ray detection data, acquired from an external device such as the below-described detection apparatus according to the present embodiment, the projection data in which parallel X-ray detection data has been converted or the parallel X-ray detection data processed by the image processing apparatus according to the present embodiment is not limited to that described above. For example, the image processing apparatus according to the present embodiment can also perform the processing by reading from a storage unit (described below) projection data in which parallel X-ray detection data has been converted, or parallel X-ray detection data, that is stored in a storage unit (described below) included in the apparatus (the image processing apparatus according to the present embodiment) or stored on an external storage medium, for example.

More specifically, the image processing apparatus according to the present embodiment forms an X-ray image by reconstituting three-dimensional data from the projection data.

Here, examples of the processing used by the image processing apparatus according to the present embodiment to reconstitute three-dimensional data from the projection data include successive approximation methods, such as ML-EM (maximum likelihood-expectation maximization), OS-EM (ordered subsets-expectation maximization), and MAP-EM (maximum a posteriori-expectation maximization). It is noted that the processing performed to reconstitute three-dimensional data from the projection data according to the present embodiment is obviously not limited to processing that uses the successive approximation methods mentioned above.

In processing using a successive approximation method like those mentioned above, a value close to the correct value is obtained by repeated projection of a reconstituted image and reverse-projection of an image (corrected image) in which the reconstituted image has been corrected. Therefore, the image processing apparatus according to the present embodiment can form a highly accurate X-ray image by performing processing that uses a successive approximation method like those mentioned above as the processing to reconstitute three-dimensional data from projection data.

Therefore, the image processing apparatus according to the present embodiment can achieve a higher quality X-ray image.

Further, as described above, the image processing apparatus according to the present embodiment forms an X-ray image based on parallel X-ray detection data by processing projection data in which parallel X-ray detection data has been converted. Here, in the projection data in which parallel X-ray detection data has been converted, there is no mixing of the data of the plurality of layers of the target, as is the case in the above-described projection data in which X-ray detection data representing a detection result of cone beam or fan beam X-rays has been converted. This is because projection data in which parallel X-ray detection data has been converted is not affected by the above-described widening and unevenness of the detection intensity resulting from a cone beam or a fan beam.

Therefore, by processing projection data in which parallel X-ray detection data has been converted, the image processing apparatus according to the present embodiment does not have to perform processing to reduce the effects of a cone beam or a fan beam, such as geometric correction, distortion correction, noise removal and the like.

Accordingly, the image processing apparatus according to the present embodiment can reduce the calculation costs for forming an X-ray image more than when processing the above-described X-ray detection data that represents a detection result of cone beam or fan beam X-rays.

Further, since the image processing apparatus according to the present embodiment does not have to perform processing to reduce the effects of a cone beam or a fan beam, such as geometric correction, distortion correction, noise removal and the like, approximation or image deterioration resulting from processing to reduce the effects of a cone beam or a fan beam is prevented. Therefore, the image processing apparatus according to the present embodiment can achieve a higher quality X-ray image.

In addition, by processing projection data in which parallel X-ray detection data has been converted, since there is no mixing of the data of the respective layers of the target in the projection data, deterioration in the accuracy of the X-ray image is prevented even if the image processing apparatus according to the present embodiment processes only the parallel X-ray detection data corresponding to a specific layer of the target. Namely, by processing projection data in which parallel X-ray detection data has been converted, with the image processing apparatus according to the present embodiment it is possible to process only the parallel X-ray detection data corresponding to a specific layer of the target.

Therefore, the image processing apparatus according to the present embodiment is capable of performing processing (e.g., processing for dividing the projection data and forming an X-ray image for each piece of divided projection data (described below)) in parallel. Further, since the image processing apparatus according to the present embodiment can form successive X-ray images each time projection data is acquired (described below), for example, the amount of memory that is used in one calculation is substantially reduced.

(2) Processing Performed in the Image Processing Method According to the Present Embodiment Next, the processing performed in the image processing method according to the present embodiment will be described in more detail.

In the following, the processing performed in the image processing method according to the present embodiment will be described based on an example in which the image processing apparatus according to the present embodiment processes projection data in which parallel X-ray detection data has been converted by an external device. It is noted that when the image processing apparatus according to the present embodiment processes parallel X-ray detection data, the image processing apparatus according to the present embodiment converts the parallel X-ray detection data into projection data, for example, and processes the converted projection data.

(2-1) First Example of the Processing Performed in the Image Processing Method According to the Present Embodiment FIG. 1 is a flow diagram illustrating a first example of the processing performed in an image processing method according to the present embodiment performed by an image processing apparatus according to the present embodiment.

The image processing apparatus according to the present embodiment determines whether projection data has been acquired (S100). The image processing apparatus according to the present embodiment determines that projection data has been acquired if all of the projection data corresponding to the target has been read into a RAM (random-access memory), for example.

If it is determined in step S100 that projection data has not been acquired, the image processing apparatus according to the present embodiment does not proceed to the next processing step until projection data is acquired.

Further, if it is determined in step S100 that projection data has been acquired, the image processing apparatus according to the present embodiment sets the image represented by the projection data as projection image P, and sets an initial reconstituted image $I_0$ (S102).

Here, although the image processing apparatus according to the present embodiment sets the initial reconstituted image $I_0$ by generating as the initial reconstituted image $I_0$ an image in which the pixel values of all of the pixels are positive, such as an image in which the pixel values of all of the pixels are indicated as "1", for example, the processing for setting the initial reconstituted image $I_0$ that is performed in the present embodiment is not limited to this. For example, in order to complete the below-described reconstitution processing more rapidly, the image processing apparatus according to the present embodiment may set an image reconstituted by a FBP (filtered back-projection) method as the initial reconstituted image $I_0$. Further, the image processing apparatus according to the present embodiment can also, for example, set an arbitrary image in which the pixel values are positive as the initial reconstituted image $I_0$.

When the processing of step S102 has been performed, the image processing apparatus according to the present embodiment performs reconstitution processing for forming an X-ray image (S 104).

Figure 2:
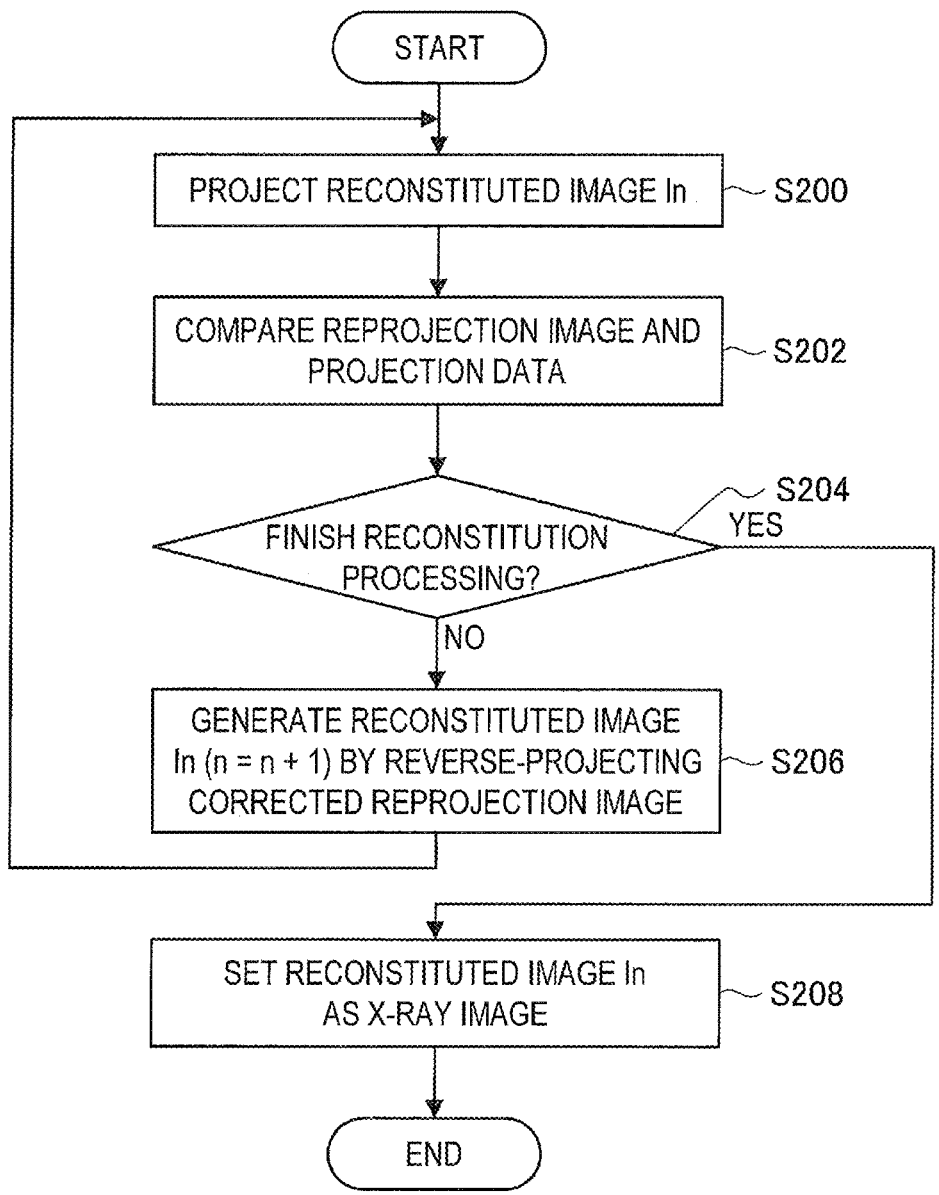
FIG. 2 is a flow diagram illustrating an example of reconstitution processing performed by the image processing apparatus according to an embodiment of the present disclosure.

FIG. 2 is a flow diagram illustrating an example of reconstitution processing performed by the image processing apparatus according to the present embodiment.

The image processing apparatus according to the present embodiment projects a reconstituted image $I_n$ (wherein n denotes an integer of 0 or more), and generates a reprojection image P' (S200). Here, the reconstituted image $I_n$ that is initially projected by the image processing apparatus according to the present embodiment is the initial reconstituted image $I_0$ set in step S102 of FIG. 1.

When the processing of step S200 has been performed, the image processing apparatus according to the present embodiment compares the reprojection image P' and the projection image P, for example, and calculates a ratio between the reprojection image P' and the projection image P (S202).

When the ratio between the reprojection image P' and the projection image P has been calculated in step S202, the image processing apparatus according to the present embodiment determines whether to finish the reconstitution processing (S204). The image processing apparatus according to the present embodiment determines that the reconstitution processing is to be finished when, for example, the ratio between the reprojection image P' and the projection image P calculated in step S202 is equal to or less than a predetermined set value (or less than a predetermined value).

If it is not determined in step S204 to finish the reconstitution processing, the image processing apparatus according to the present embodiment reverse-projects the reprojection image P' (correction value) using the ratio between the reprojection image P' and the projection image P to generate a new reconstituted image $I_n$ (n=n+1) (S206). Then, the image processing apparatus according to the present embodiment repeats the processing from step S200.

Further, if it is determined in step S204 to finish the reconstitution processing, the image processing apparatus according to the present embodiment sets the reconstituted image $I_n$ as the X-ray image (a so-called reconstituted layer image) (S208). Then, the image processing apparatus according to the present embodiment finishes the reconstitution processing.

The image processing apparatus according to the present embodiment performs the processing illustrated in FIG. 2, for example, as the reconstitution processing according to the present embodiment.

Here, when the image processing apparatus according to the present embodiment uses ML-EM, which is a basic successive approximation method that uses maximum likelihood estimation, the reconstitution processing according to the present embodiment is represented by the following formula 1, for example.

$$\lambda_j^{(k+1)} = \frac{\lambda_j^{(k)}}{\sum_{i=1}^{n} C_{ij}} \cdot \sum_{i=1}^{n} \frac{y_i \cdot C_{ij}}{\sum_{j'=1}^{m} C_{ij'} \cdot \lambda_{j'}^{(k)}} \quad \text{(Formula 1)}$$

The "i" in formula 1 represents the coordinates of the reconstituted image (the coordinates corresponding to the position of the target), the "j" in formula 1 represents the coordinates of the projection image P, and the "k" in formula 1 represents the number of repetitions. Further, the "$C_{ij}$" in formula 1 represents the "detection rate", which is the probability of the voxel of coordinate i in the target being detected by a detector corresponding to coordinate j of the projection image P.

Therefore, for example, to reconstitute a given layer by a successive approximation method, one calculation cycle can be carried out by plugging all of the voxels of that layer and the values of the detection positions corresponding to those voxels. Accordingly, when reconstituting an X-ray image corresponding to a three-dimensional object (target), the reconstituted image and the projection image P based on the projection data are three-dimensional, so that the calculation represented in formula 1 can be carried out on all of the voxels in three dimensions.

Figure 3:
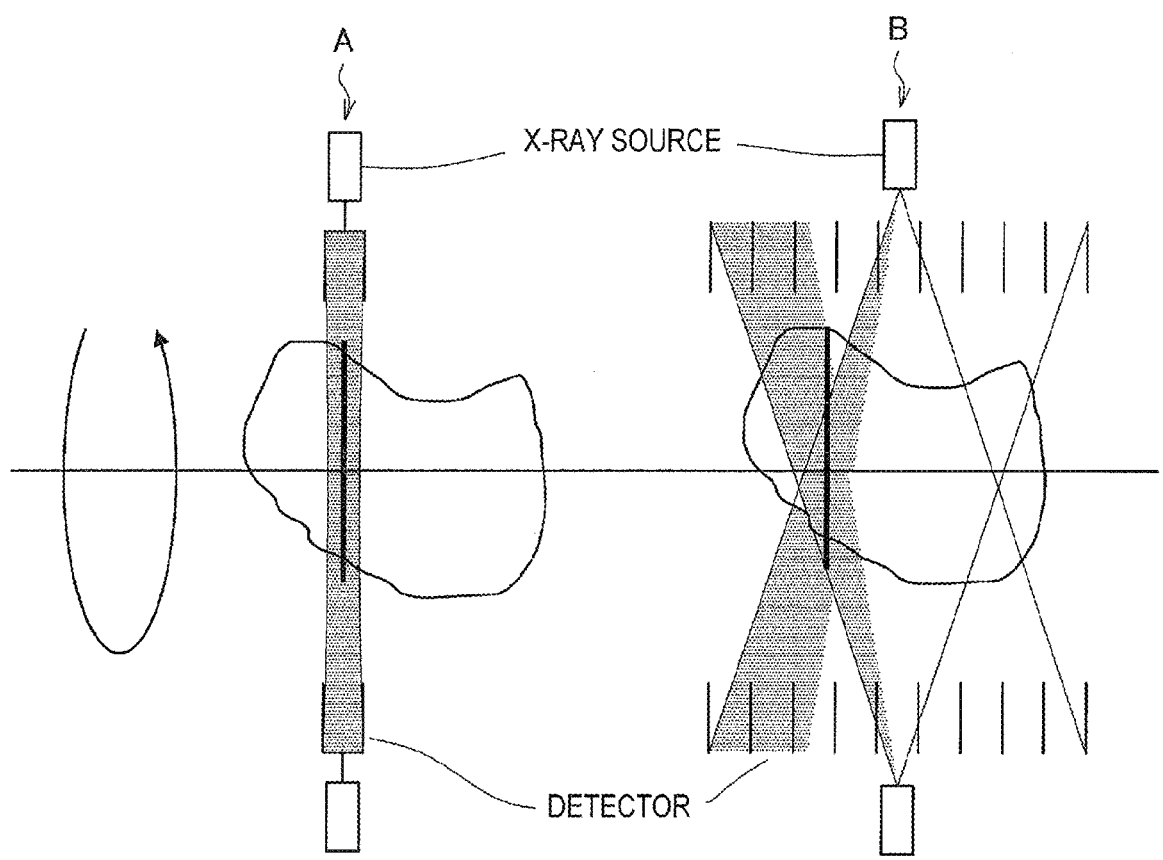
FIG. 3 is an explanatory diagram illustrating the processing performed in the image processing method according to an embodiment of the present disclosure.

FIG. 3 is an explanatory diagram illustrating the processing performed in the image processing method according to the present embodiment. FIG. 3 illustrates an example in a typical CT of the correspondence among the position of the X-ray source, the position of the target through which the X-rays pass, and the position of the detector. Symbol A in FIG. 3 illustrates an example in a single-slice type CT apparatus of the correspondence among the position of the X-ray source, the position of the target through which the X-rays pass, and the position of the detector. Further, symbol B in FIG. 3 illustrates an example in a multi-slice type CT apparatus of the correspondence among the position of the X-ray source, the position of the target through which the X-rays pass, and the position of the detector.

For the single-slice type CT apparatus illustrated by A in FIG. 3, since one layer and one array of detectors correspond to each other on a one-to-one basis, the successive calculations performed in the above reconstitution processing can be performed layer by layer. Namely, in the case of the single-slice type CT apparatus illustrated by A in FIG. 3, in formula 1 a two-dimensional×two-dimensional calculation can be performed. Therefore, when reconstituting the X-ray image using the single-slice type CT apparatus illustrated by A in FIG. 3, the calculation costs to form the X-ray image are smaller than the calculation costs to form the X-ray image when reconstituting an X-ray image using the multi-slice type CT apparatus employing an X-ray source that outputs cone beam X-rays like that illustrated by B in FIG. 3. However, with the single-slice type CT apparatus illustrated by A in FIG. 3, the larger the detection area of the target, the longer it takes to generate the X-ray image.

Further, for recent CT apparatuses, in order to increase the detection area and shorten the time, a multi-slice type like that illustrated by B in FIG. 3 is mainstream. Here, for a multi-slice type CT apparatus, an X-ray source that outputs cone beam X-rays is used, as illustrated by B of FIG. 3.

When an X-ray source that outputs cone beam X-rays is used as illustrated by B of FIG. 3, when an attempt is made to reconstitute the X-ray image corresponding to a given layer, the width of the detector corresponding to the X-rays that pass through that layer surface increases. In addition, when the X-ray source and the detector are rotated by a gantry and the like configuring the CT apparatus, the position of the detector that passes through a given voxel of the target changes depending on the angle of rotation.

Therefore, when an X-ray source that outputs cone beam X-rays is used as illustrated by B of FIG. 3, when reconstituting the X-ray image corresponding to the layer surface, all of the relevant voxels and the detectors are used in the calculation. Namely, when reconstituting an X-ray image using an X-ray source that outputs cone beam X-rays as illustrated by B of FIG. 3, all of the voxels and the detectors that have an effect on each other are used in all the calculations even when trying to reconstitute the X-ray image corresponding to a given specific layer surface.

Therefore, when reconstituting an X-ray image using an X-ray source that outputs cone beam X-rays as illustrated by B of FIG. 3, the value of all the voxels in the three-dimensional information about the target and the value of all the detectors are used in a given single calculation. Namely, when reconstituting an X-ray image using an X-ray source that outputs cone beam X-rays as illustrated by B of FIG. 3, the calculation amount of the detection probability $C_{ij}$ in formula 1 increases.

Figure 4:
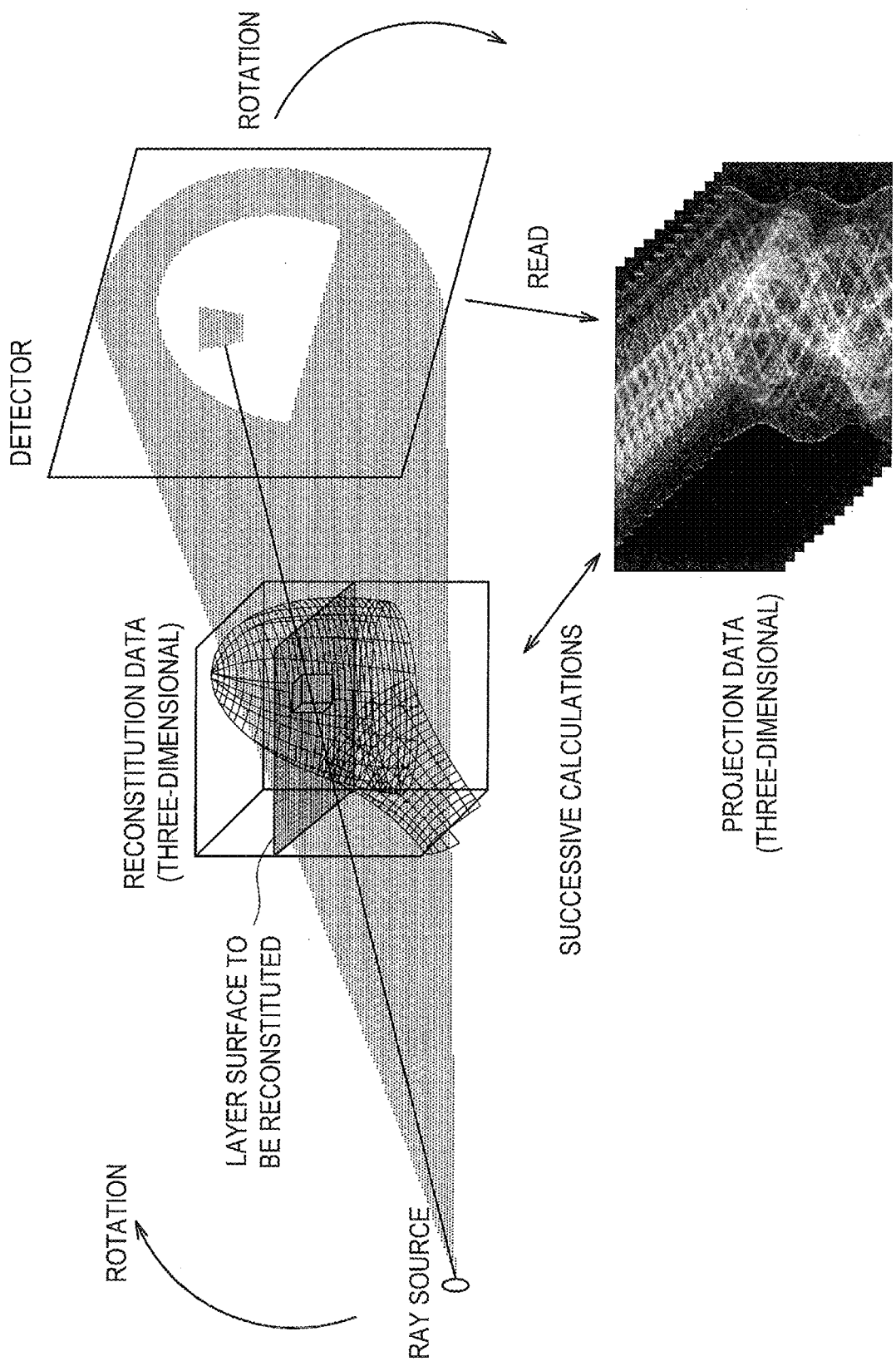
FIG. 4 is an explanatory diagram illustrating the processing performed in the image processing method according to an embodiment of the present disclosure.

FIG. 4, which is an explanatory diagram illustrating the processing performed in the image processing method according to the present embodiment, illustrates the outline of the processing that is performed when reconstituting an X-ray image using a cone beam X-ray source.

As illustrated in FIG. 4, when reconstituting an X-ray image using an X-ray source that outputs cone beam X-rays as illustrated by B of FIG. 3, correspondence between three-dimensional data×three-dimensional data is repeatedly calculated based on formula 1. Therefore, when reconstituting an X-ray image using an X-ray source that outputs cone beam X-rays as illustrated by B of FIG. 3, the calculation amount is very large. Further, even when reconstituting an X-ray image using a fan beam X-ray source, similar to when reconstituting an X-ray image using an X-ray source that outputs cone beam X-rays as illustrated by B of FIG. 3, the calculation amount relating to the reconstitution of the X-ray image is very large.

Therefore, as described above, when forming an X-ray image having greater accuracy by processing projection data in which X-ray detection data representing a result that X-rays output from an X-ray source that outputs cone beam X-rays or an X-ray source that outputs fan beam X-rays have been detected has been converted, the calculation costs for forming the X-ray image become very large.

Figure 5:
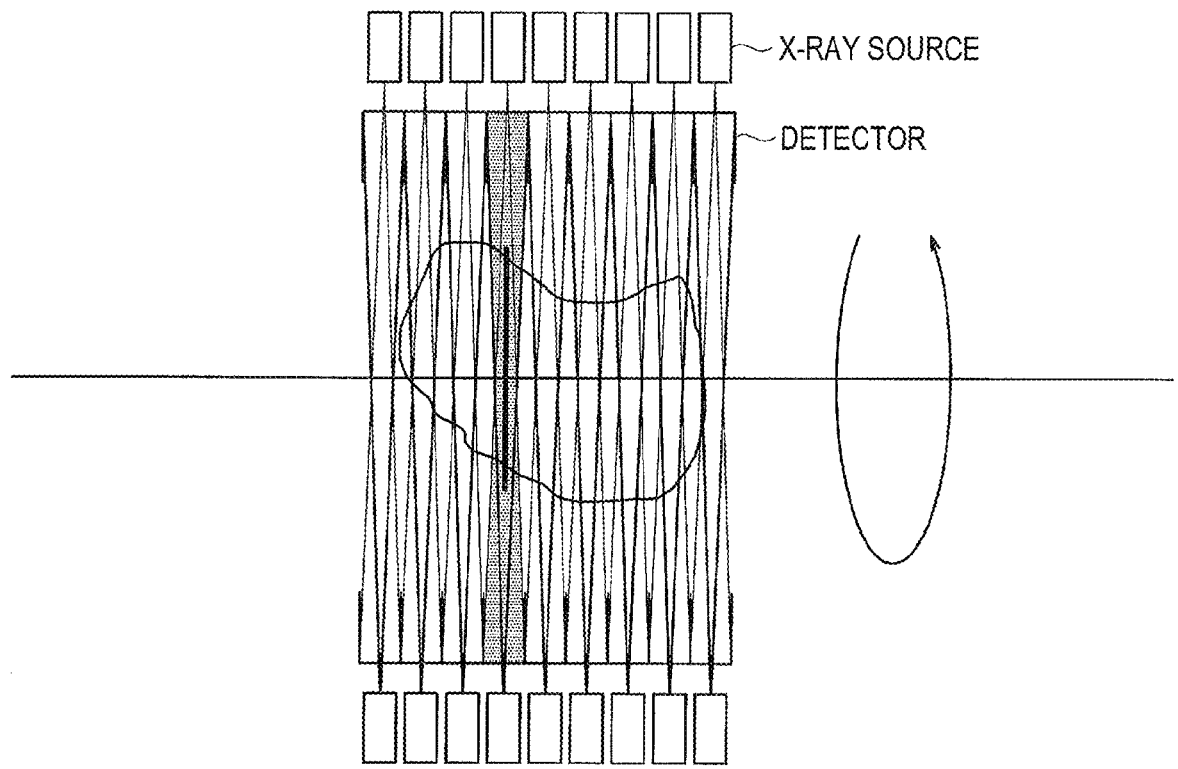
FIG. 5 is an explanatory diagram illustrating the processing performed in the image processing method according to an embodiment of the present disclosure.

FIG. 5, which is an explanatory diagram illustrating processing performed in the image processing method according to the present embodiment, illustrates an example of a multi-slice type CT apparatus in which an X-ray source that outputs parallel beam X-rays is used.

As illustrated in FIG. 5, when an X-ray source that outputs parallel beam X-rays is used, since X-rays are irradiated from an X-ray source parallel to the array of detectors, mixing of the layer data among the layers is eliminated, so that each cross-section and each detector array are independent, and the correspondence between the cross-sections and the detectors is on a one-to-one basis. Further, as described above, the image processing apparatus according to the present embodiment forms an X-ray image based on X-ray detection data by processing projection data in which X-ray detection data representing a detection result of parallel beam X-rays output from an X-ray source has been converted.

Therefore, in the reconstitution processing according to the present embodiment illustrated in FIG. 2, the image processing apparatus according to the present embodiment can perform the successive calculations for reconstitution on a per layer basis in a closed state. Further, since the reconstitution calculations are also two-dimensional×two-dimensional, the calculation amount that is performed in one go can be substantially reduced. In addition, the calculation amount of the detection probability $C_{ij}$ in formula 1 can be reduced by a lot more than when reconstituting an X-ray image using an X-ray source that outputs cone beam X-rays as illustrated by B of FIG. 3, for example.

The image processing apparatus according to the present embodiment performs the processing illustrated in FIG. 1, for example, as the processing performed in the image processing method according to the present embodiment.

Here, in the projection data in which parallel X-ray detection data has been converted that is processed by the image processing apparatus according to the present embodiment in the processing illustrated in FIG. 1, there is no mixing of data of the plurality of layers of the target, as is the case with the above-described projection data in which X-ray detection data representing a detection result of cone beam or fan beam X-rays has been converted. Namely, when performing the processing illustrated in FIG. 1, for example, the image processing apparatus according to the present embodiment does not have to perform processing to reduce the effects of a cone beam or a fan beam, such as geometric correction, distortion correction, noise removal and the like. Further, the calculation amount relating to the reconstitution processing performed by the image processing apparatus according to the present embodiment is reduced by a lot more than when processing the above-described projection data in which X-ray detection data representing a detection result of cone beam or fan beam X-rays has been converted. Therefore, when performing the processing illustrated in FIG. 1, for example, deterioration resulting from the processing to reduce the effects of a cone beam or a fan beam is prevented. Further, the calculation costs for forming an X-ray image can be reduced more than when processing the above-described X-ray detection data that represents a detection result of cone beam or fan beam X-rays.

Therefore, by performing the processing illustrated in FIG. 1, for example, the image processing apparatus according to the present embodiment can achieve a higher quality X-ray image while reducing the calculation costs for forming an X-ray image even further.

Further, for example, in the processing illustrated in FIG. 1, the image processing apparatus according to the present embodiment performs processing that uses a successive approximation method, such as processing using the ML-EM method represented in formula 1, for example, as the reconstitution processing for forming an X-ray image. Therefore, since a highly accurate X-ray image can be formed by performing the processing illustrated in FIG. 1, for example, a higher quality X-ray image can be achieved.

It is noted that the processing performed in the image processing method according to the present embodiment that is performed by the image processing apparatus according to the present embodiment is not limited to the processing according to the first example illustrated in FIG. 1.

As described above, by processing projection data in which parallel X-ray detection data has been converted, there is no mixing in the projection data of the data from respective layers in the target. Therefore, a deterioration in the accuracy of the X-ray image is prevented even if the image processing apparatus according to the present embodiment processes only the parallel X-ray detection data corresponding to a specific layer of the target. Namely, by processing projection data in which parallel X-ray detection data has been converted, with the image processing apparatus according to the present embodiment it is possible to process only the parallel X-ray detection data corresponding to a specific layer of the target.

Therefore, the image processing apparatus according to the present embodiment can, for example, divide the projection data and form an X-ray image for each piece of divided projection data (the parallel processing according to the present embodiment). Further, the image processing apparatus according to the present embodiment can also form successive X-ray images each time projection data is acquired (the successive processing according to the present embodiment).

Figure 6:
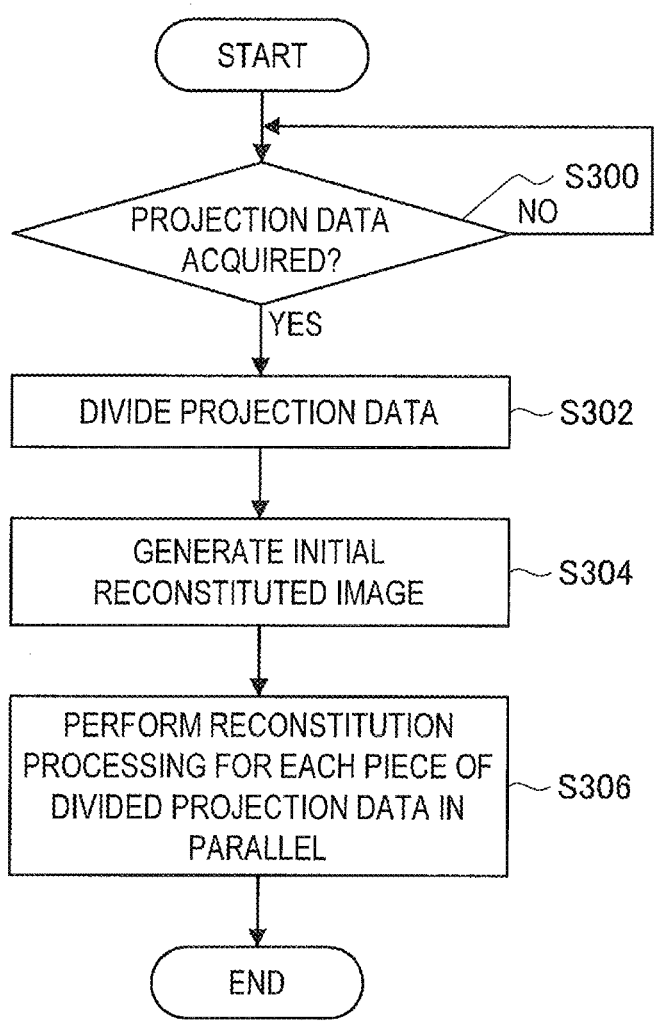
FIG. 6 is a flow diagram illustrating a second example of the processing performed in the image processing method according to an embodiment of the present disclosure performed by the image processing apparatus according to an embodiment of the present disclosure.

(2-2) Second Example of the Processing Performed in the Image Processing Method According to the Present Embodiment FIG. 6 is a flow diagram illustrating a second example of the processing performed in the image processing method according to the present embodiment by the image processing apparatus according to the present embodiment. Here, FIG. 6 illustrates an example of the parallel processing according to the present embodiment.

Similar to step S100 of FIG. 1, the image processing apparatus according to the present embodiment determines whether projection data has been acquired (S300). If it is determined in step S300 that projection data has not been acquired, the image processing apparatus according to the present embodiment does not proceed to the next processing step until projection data is acquired.

Further, if it is determined in step S300 that projection data has been acquired, the image processing apparatus according to the present embodiment divides the projection data (S302). Here although the image processing apparatus according to the present embodiment divides the projection data on a per layer basis, for example, the units that the image processing apparatus according to the present embodiment divides the projection data into are not especially limited. Further, the units into which the image processing apparatus according to the present embodiment divides the projection data may be, for example, a single unit, or a mixture of a plurality of units. The image processing apparatus according to the present embodiment sets an image represented by each piece of divided projection data as the projection image P.

Further, if it is determined in step S300 that projection data has been acquired, the image processing apparatus according to the present embodiment sets an initial reconstituted image $I_0$ corresponding to each piece of divided projection data (S304). Here, the image processing apparatus according to the present embodiment sets the initial reconstituted image $I_0$ in the same manner as in step S102 of FIG. 1.

It is noted that although in FIG. 6 an example is illustrated in which the processing of step S304 is carried out after the processing step S302, the processing of step S302 and the processing step S304 can be performed independently. Therefore, the image processing apparatus according to the present embodiment can perform the processing of step S302 and the processing step S304 in synchronization, for example.

When the processing steps S302 and S304 has been performed, the image processing apparatus according to the present embodiment performs in parallel the reconstitution processing for forming an X-ray image for each piece of divided projection data (S306). Here, the image processing apparatus according to the present embodiment performs the reconstitution processing for forming X-ray images in the same manner as in step S104 of FIG. 1, for example.

The image processing apparatus according to the present embodiment performs the processing illustrated in FIG. 6, for example, as the processing performed in the image processing method according to the present embodiment.

Here, in the projection data that is processed by the image processing apparatus according to the present embodiment in the processing illustrated in FIG. 6, similar to the processing according to the first example illustrated in FIG. 1, there is no mixing of data of the plurality of layers of the target. Namely, similar to the processing according to the first example illustrated in FIG. 1, when performing the processing illustrated in FIG. 6, for example, the image processing apparatus according to the present embodiment does not have to perform processing to reduce the effects of a cone beam or a fan beam, such as geometric correction, distortion correction, noise removal and the like. Further, similar to the processing according to the first example illustrated in FIG. 1, the calculation amount relating to the reconstitution processing performed by the image processing apparatus according to the present embodiment is reduced by a lot more than when processing the above-described projection data in which X-ray detection data representing a detection result of cone beam or fan beam X-rays has been converted.

Therefore, similar to the processing according to the first example illustrated in FIG. 1, by performing the processing illustrated in FIG. 6, for example, the image processing apparatus according to the present embodiment can achieve a higher quality X-ray image while reducing the calculation costs for forming an X-ray image even further.

Further, in the processing illustrated in FIG. 6, the dividing of the projection data into respective layers and the reconstitution processing corresponding to each piece of projection data are performed in parallel.

Therefore, the image processing apparatus according to the present embodiment can shorten the processing time (calculation time) taken for the reconstitution processing more than when an X-ray image is reconstituted using an X-ray source that outputs cone beam or fan beam X-rays, for example. In addition, similar to the processing according to the first example illustrated in FIG. 1, since there is no mixing of the data of the plurality of layers of the target in the projection data processed by the image processing apparatus according to the present embodiment, deterioration in the accuracy of the X-ray image is prevented even if the image processing apparatus according to the present embodiment processes only the parallel X-ray detection data corresponding to a specific layer of the target.

Figure 7:
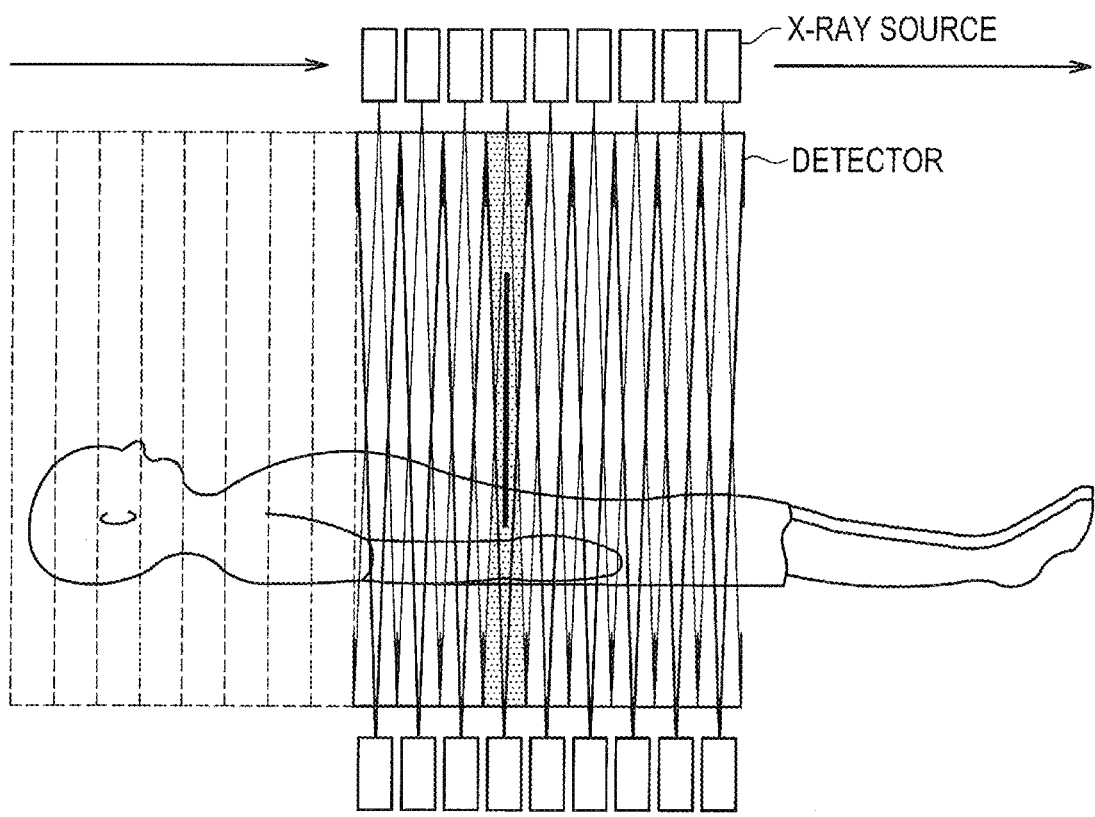
FIG. 7 is an explanatory diagram illustrating processing performed in the image processing method according to an embodiment of the present disclosure.

(2-3) Third Example of the Processing Performed in the Image Processing Method According to the Present Embodiment FIG. 7 is an explanatory diagram illustrating the processing performed in the image processing method according to the present embodiment. FIG. 7 illustrates an example in a helical scanning type CT apparatus, or in a non-helical scanning type CT apparatus, for example, of the correspondence among the position of the X-ray source, the position of the target through which the X-rays pass, and the position of the detector. Further, a person is shown in FIG. 7 as the target.

In a helical scanning type CT apparatus or a non-helical scanning type CT apparatus like that illustrated in FIG. 7, when an X-ray source that outputs cone beam X-rays is used as illustrated by B of FIG. 3, reconstitution processing like that illustrated in FIG. 2 is not performed until all of the scans of the target are finished. This is because, as described above, when reconstituting an X-ray image using an X-ray source that outputs cone beam X-rays, all of the voxels and the detectors that have an effect on each other are used in all the calculations even when trying to reconstitute the X-ray image corresponding to a given specific layer surface.

In contrast, in the projection data in which parallel X-ray detection data has been converted that is processed by the image processing apparatus according to the present embodiment, there is no mixing of data of the plurality of layers of the target, as is the case with the above-described projection data in which X-ray detection data representing a detection result of cone beam or fan beam X-rays has been converted. Therefore, as described above, a deterioration in the accuracy of the X-ray image is prevented even if the image processing apparatus according to the present embodiment processes only the parallel X-ray detection data corresponding to a specific layer of the target. Namely, a deterioration in the accuracy of the X-ray image to be formed does not occur even if successive X-ray images are formed each time projection data is acquired, for example.

Accordingly, as the processing according to the third example of the image processing method according to the present embodiment, an example will be described of processing that can realize the successive processing according to the present embodiment.

Figure 8:
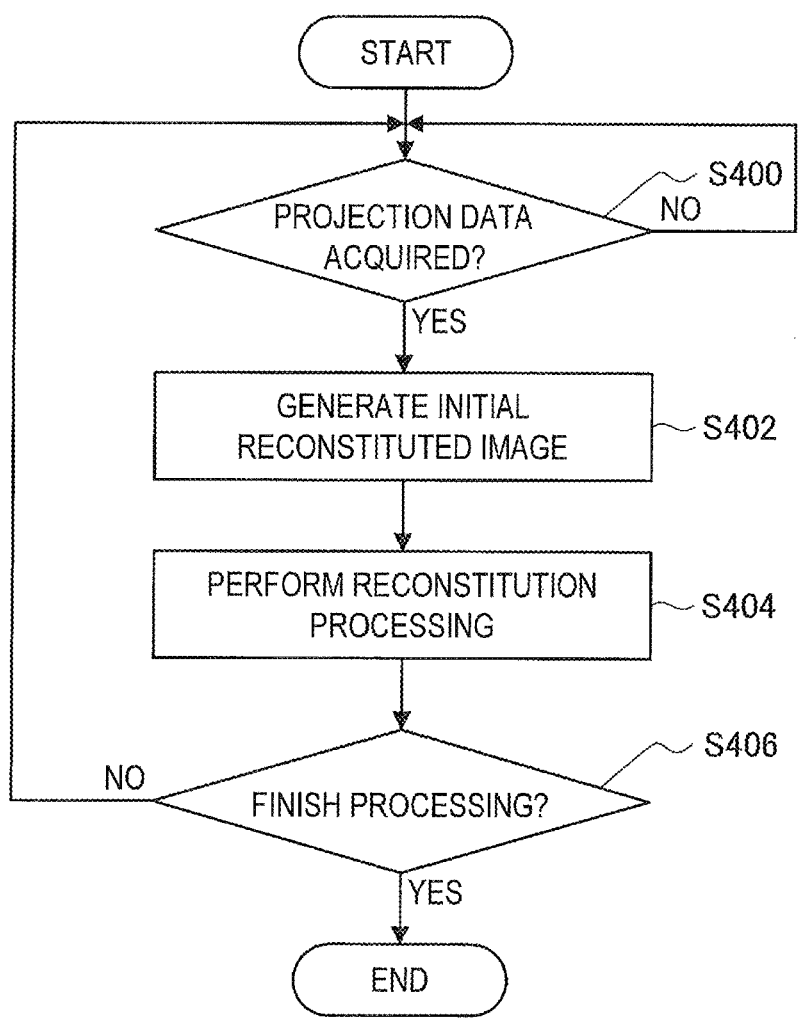
FIG. 8 is a flow diagram illustrating a third example of the processing performed in the image processing method according to an embodiment of the present disclosure performed by the image processing apparatus according to an embodiment of the present disclosure.

FIG. 8 is a flow diagram illustrating a third example of the processing performed in the image processing method according to the present embodiment performed by the image processing apparatus according to present embodiment. Here, FIG. 8 illustrates an example of the successive processing according to the present embodiment.

The image processing apparatus according to the present embodiment determines whether projection data has been acquired (S400). The image processing apparatus according to the present embodiment determines that projection data has been acquired if projection data transmitted from an external device has been received, and the received projection data read into the RAM or the like, or if projection data stored in a storage unit (described below) has been read from the storage unit (described below), and the read projection data read into the RAM or the like, for example.

If it is determined in step S400 that projection data has not been acquired, the image processing apparatus according to the present embodiment does not proceed to the next processing step until projection data is acquired.

Further, if it is determined in step S400 that projection data has been acquired, the image processing apparatus according to the present embodiment sets an initial reconstituted image $I_0$ in the same manner as in step S102 of FIG. 1 (S402).

When the processing step S402 has been performed, the image processing apparatus according to the present embodiment performs the reconstitution processing for forming an X-ray image in the same manner as in step S104 of FIG. 1 (S404).

When the processing step S404 has been performed, the image processing apparatus according to the present embodiment determines whether to finish the processing performed in the image processing method according to the present embodiment (S406). Here, when processing projection data based on parallel X-ray detection data representing a detection result in a helical scanning type CT apparatus or a non-helical scanning type CT apparatus like that illustrated in FIG. 7, the image processing apparatus according to the present embodiment determines, for example, to finish the processing performed in the image processing method according to the present embodiment when a signal indicating that scanning has finished transmitted from an external device, such as the CT apparatus, is received. Further, if projection data stored in a storage unit (described below) or the like is processed, the image processing apparatus according to the present embodiment determines to finish the processing performed in the image processing method according to the present embodiment when, for example, all of projection data (e.g., projection data formed into groups based on metadata and the like) corresponding to a given target has been read from the storage unit (described below).

If it is not determined in step S406 to finish the processing performed in the image processing method according to the present embodiment, the image processing apparatus according to the present embodiment repeats the processing from step S400. Further, if it is determined in step S406 to finish the processing performed in the image processing method according to the present embodiment, the image processing apparatus according to the present embodiment finishes the processing performed in the image processing method according to the present embodiment.

The image processing apparatus according to the present embodiment performs the processing illustrated in FIG. 8, for example, as the processing performed in the image processing method according to the present embodiment.

Here, in the projection data that is processed by the image processing apparatus according to the present embodiment in the processing illustrated in FIG. 8, similar to the processing according to the first example illustrated in FIG. 1, there is no mixing of data of the plurality of layers of the target. Namely, similar to the processing according to the first example illustrated in FIG. 1, when performing the processing illustrated in FIG. 8, for example, the image processing apparatus according to the present embodiment does not have to perform processing to reduce the effects of a cone beam or a fan beam, such as geometric correction, distortion correction, noise removal and the like. Further, similar to the processing according to the first example illustrated in FIG. 1, the calculation amount relating to the reconstitution processing performed by the image processing apparatus according to the present embodiment is reduced by a lot more than when processing the above-described projection data in which X-ray detection data representing a detection result of cone beam or fan beam X-rays has been converted.

Therefore, similar to the processing according to the first example illustrated in FIG. 1, by performing the processing illustrated in FIG. 8, for example, the image processing apparatus according to the present embodiment can achieve a higher quality X-ray image while reducing the calculation costs for forming an X-ray image even further.

In addition, similar to the processing according to the first example illustrated in FIG. 1, since there is no mixing of the data of the plurality of layers of the target in the projection data processed by the image processing apparatus according to the present embodiment, deterioration in the accuracy of the X-ray image is prevented even if only the parallel X-ray detection data corresponding to a specific layer of the target is processed. Namely, since the image processing apparatus according to the present embodiment can independently perform processing on each layer surface, in the processing illustrated in FIG. 8, the image processing apparatus according to the present embodiment forms successive X-ray images each time projection data is acquired.

Therefore, in a helical scanning type CT apparatus or a non-helical scanning type CT apparatus like that illustrated in FIG. 7, the image processing apparatus according to the present embodiment perform the calculations relating to the formation of the X-ray image, such as a reconstitution calculation, in order from the portions for which scanning has finished. For example, the calculations relating to the formation of the X-ray image can be completed along with as the finishing of the CT scanning.

Further, since the image processing apparatus according to the present embodiment forms successive X-ray images each time projection data is acquired, the amount of memory that is used in one calculation is substantially reduced.

(Image Processing Apparatus According to the Present Embodiment)

Next, an example of the configuration of an image processing apparatus according to the present embodiment that is capable of performing the processing performed in the above-described image processing method according to the present embodiment will be described.

Figure 9:
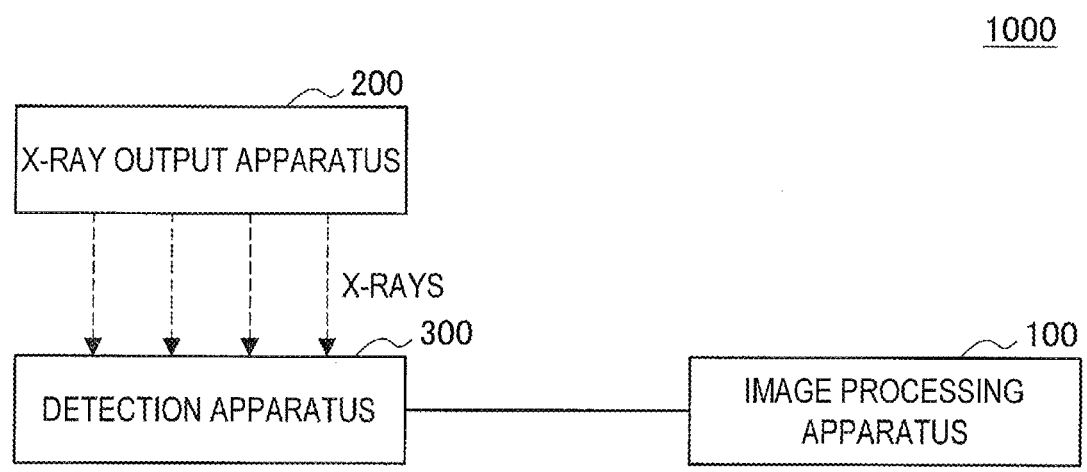
FIG. 9 is an explanatory diagram illustrating an example of an image processing system according to an embodiment of the present disclosure.

(I) Example of the Configuration of the Image Processing System According to the Present Embodiment Before describing an example of the configuration of the image processing apparatus according to the present embodiment, an example of the image processing system according to the present embodiment that has the image processing apparatus according to the present embodiment will be described. FIG. 9 is an explanatory diagram illustrating an example of an image processing system 1000 according to the present embodiment. The image processing system 1000 has, for example, an image processing apparatus 100, an X-ray output apparatus 200, and a detection apparatus 300.

The X-ray output apparatus 200 includes, for example, an X-ray source (not illustrated), for outputting parallel beam X-rays. Here, examples of the X-ray source included in the X-ray output apparatus 200 include an X-ray tube, which is an electron tube for generating X-rays, a colimeter that forms parallel beam X-rays from X-rays generated by an X-ray tube, and a planar source in which a plurality of X-ray tubes are arranged on a flat face.

It is noted that the configuration of the X-ray output apparatus 200 is not limited to that described above. For example, the X-ray output apparatus 200 is configured from a MPU (micro-processing unit), various processing circuits and the like. Further, the X-ray output apparatus 200 may also include a control unit (not illustrated) for controlling the generation of X-rays by the X-ray source, a ROM (read-only memory, not illustrated), a RAM (not illustrated) and the like.

Here, the ROM (not illustrated) included in the X-ray output apparatus 200 stores control data, such as programs and calculation parameters used by the control unit (not illustrated) included in the detection apparatus 300. The RAM included in the X-ray output apparatus 200 temporarily stores programs, for example, that are executed by the control unit (not illustrated) included in the X-ray output apparatus 200.

The detection apparatus 300, which includes a detection unit (not illustrated) that has a detector for detecting X-rays, for example, detects parallel beam X-rays and generates parallel X-ray detection data.

It is noted that the configuration of the detection apparatus 300 is not limited to that described above. For example, the detection apparatus 300 is configured from a MPU, various processing circuits and the like. Further, the detection apparatus 300 may also include a processing unit (not illustrated) for converting parallel X-ray detection data into projection data, a ROM (read-only memory, not illustrated), a RAM (not illustrated), a communication unit and the like.

Here, the ROM (not illustrated) included in the detection apparatus 300 stores control data, such as programs and calculation parameters used by the control unit (not illustrated) included in the detection apparatus 300. The RAM included in the detection apparatus 300 temporarily stores programs, for example, that are executed by the control unit (not illustrated) included in the detection apparatus 300.

The communication unit (not illustrated) included in the detection apparatus 300 is a communication device included in the detection apparatus 300, which has the role of performing wireless/wired communication with an external device, such as the image processing apparatus 100, via a network (or directly). Here, examples of the communication unit (not illustrated) included in the detection apparatus 300 include a communication antenna and an RF (radio frequency) circuit (wireless communication), an IEEE 802.15.1 port and a transmitting/receiving circuit (wireless communication), an IEEE 802.11b port and a transmitting/receiving circuit (wireless communication), or a LAN (local area network) terminal and a transmitting/receiving circuit (wired communication) and the like. Further examples of the communication unit (not illustrated) included in the detection apparatus 300 include a configuration that supports an arbitrary standard capable of performing communication, such as a USB (universal serial bus) terminal and a transmitting/receiving circuit, and an arbitrary configuration capable of communicating with an external device via a network. Examples of the network according to the embodiment of the present disclosure include a wired network such as a LAN or a WAN (wide area network), a wireless network such as a wireless LAN (wireless local area network), and wireless WAN (wireless wide area network) via a base station, or the Internet using a communication protocol such as TCP/IP (transmission control protocol/internet protocol) and the like.

The detection apparatus 300 transmits to the image processing apparatus 100, for example, the generated parallel X-ray detection data or projection data in which parallel X-ray detection data has been converted.

The image processing apparatus 100 forms an X-ray image based on parallel X-ray detection data by performing the above-described processing performed in the image processing method according to the present embodiment, and processing parallel X-ray detection data or projection data in which parallel X-ray detection data has been converted.

Here, the image processing apparatus 100 processes, for example, parallel X-ray detection data transmitted from the detection apparatus 300, or projection data transmitted from the detection apparatus 300 in which parallel X-ray detection data has been converted. It is noted that the image processing apparatus 100 can process, for example, parallel X-ray detection data stored in a storage unit (described below) or the like, or projection data stored in the storage unit (described below) or the like in which parallel X-ray detection data has been converted. Examples of parallel X-ray detection data stored in the storage unit (described below) or the like include parallel X-ray detection data generated by the detection apparatus 300 and parallel X-ray detection data generated by an external device other than the detection apparatus 300. Further, examples of projection data stored in the storage unit (described below) or the like in which parallel X-ray detection data has been converted include projection data converted by the detection apparatus 300 and projection data generated by an external device other than the detection apparatus 300.

The image processing system 1000 has, for example, the configuration illustrated in FIG. 9. In the image processing system 1000 illustrated in FIG. 9, the image processing apparatus 100 forms an X-ray image based on parallel X-ray detection data by performing the above-described processing performed in the image processing method according to the present embodiment. Therefore, based on the configuration illustrated in FIG. 9, for example, an image processing system is realized that can achieve a higher quality X-ray image while reducing the calculation costs for forming an X-ray image even further.

It is noted that the image processing system according to the present embodiment is not limited to the configuration illustrated in FIG. 9. For example, in the image processing system according to the present embodiment, the X-ray output apparatus 200 and the detection apparatus 300 may be an integrated apparatus, like a CT apparatus that utilizes X-rays or an apparatus having a tomosynthesis function in which X-rays are utilized. Further, if the X-ray output apparatus 200 and the detection apparatus 300 are an integrated apparatus, such an apparatus may include a gantry that has a rotary motor, for example.

(II) Example of the Configuration of the Image Processing Apparatus According to the Present Embodiment Next, an example of the configuration of the image processing apparatus according to the present embodiment will be described using the image processing apparatus 100 configuring the image processing system 1000 illustrated in FIG. 9 as an example.

Figure 10:
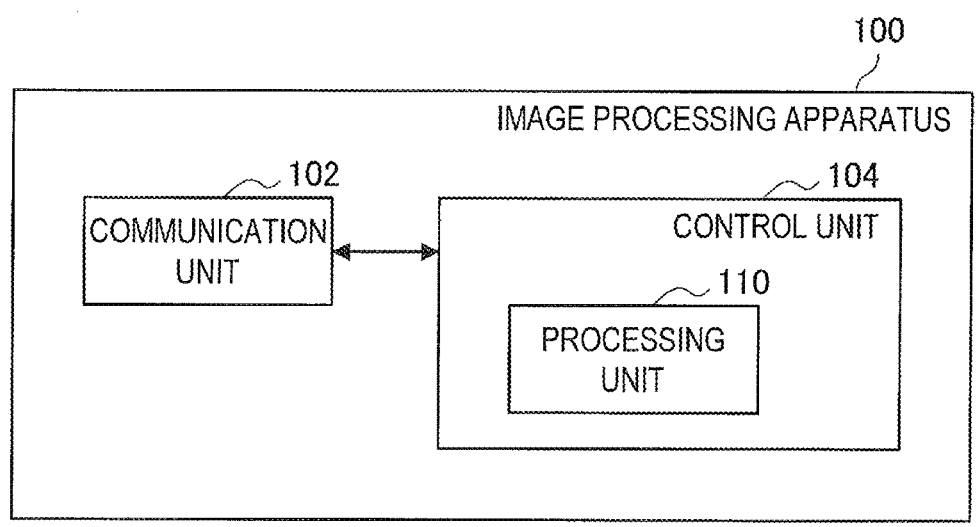
FIG. 10 is a block diagram illustrating an example of a configuration of the image processing apparatus according to an embodiment of the present disclosure.

FIG. 10 is a block diagram illustrating an example of a configuration of an image processing apparatus 100 according to an embodiment of the present disclosure. The image processing apparatus 100 includes, for example, a communication unit 102 and a control unit 104.

Further, the image processing apparatus 100 may also include, for example, a ROM (not illustrated), a RAM (not illustrated), a storage unit (not illustrated), a user-operable operation unit (not illustrated), a display unit (not illustrated) that displays various screens on a display screen and the like.

The image processing apparatus 100 connects these constituent elements to each other with a bus that serves as a data transmission path.

Here, the ROM (not illustrated) stores control data, such as programs and calculation parameters used by the control unit 104. The RAM (not illustrated) temporarily stores programs and the like that are executed by the control unit 104.

The storage unit (not illustrated) is a storage device included in the image processing apparatus 100, which stores, for example, various data such as X-ray detection data, projection data in which X-ray detection data has been converted, and applications. Here, examples of the storage unit (not illustrated) include magnetic recording media such as a hard disk, non-volatile memory such as flash memory and the like. Further, the storage unit (not illustrated) may be detachable from the image processing apparatus 100.

In addition, examples of the operation unit (not illustrated) include the below-described operation input device. Examples of the display unit (not illustrated) may include the below-described display device.

(Hardware Configuration Example of the Image Processing Apparatus 100)

Figure 11:
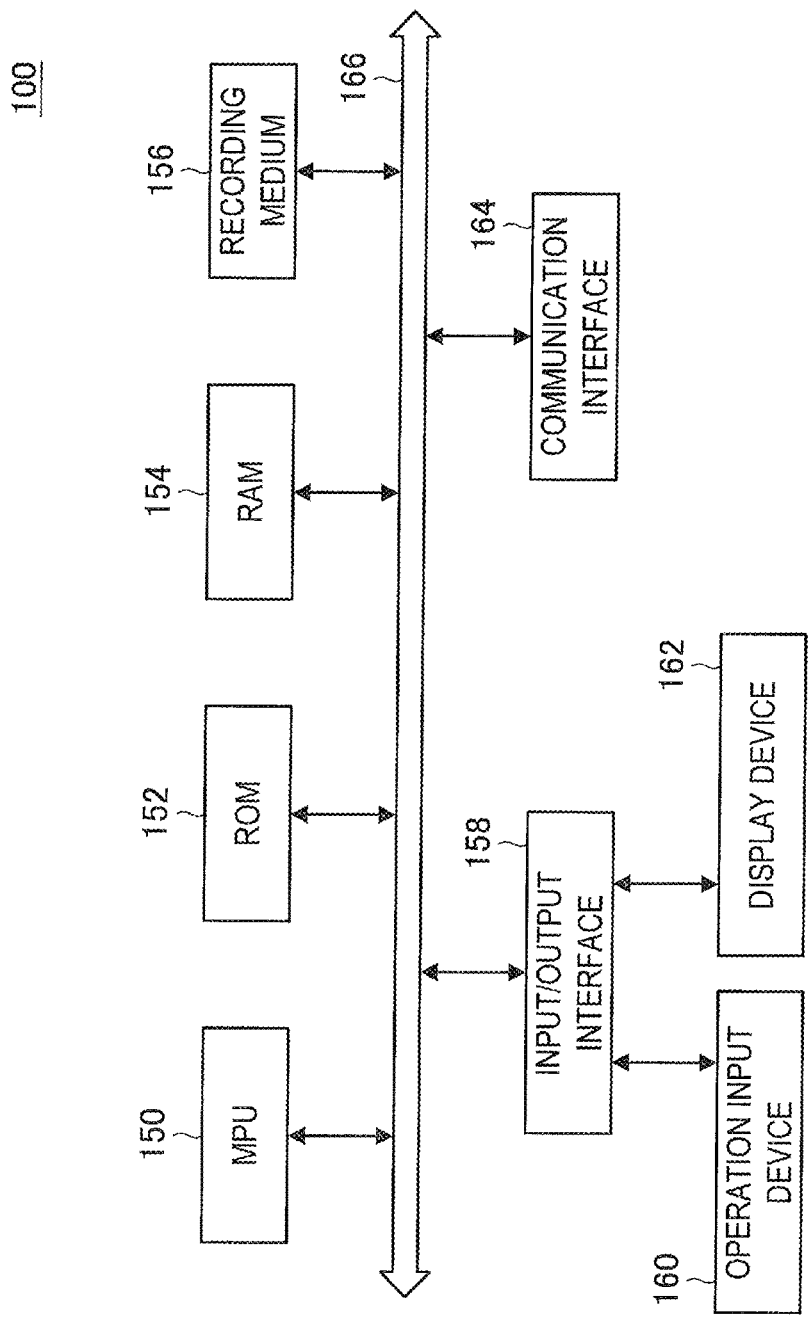
FIG. 11 is a diagram illustrating an example of a hardware configuration of the image processing apparatus according to an embodiment of the present disclosure.

FIG. 11 is an explanatory diagram illustrating an example of a hardware configuration of the image processing apparatus 100 according to an embodiment of the present disclosure. The image processing apparatus 100 includes, for example, a MPU 150, a ROM 152, a RAM 154, a recording medium 156, an input/output interface 158, an operation input device 160, a display device 162, and a communication interface 164. Further, the image processing apparatus 100 connects these constituent elements to each other with a bus 166 that serves as a data transmission path.

The MPU 150 is configured from, for example, a MPU, various processing circuits and the like. The MPU 150 functions as the control unit 104 for controlling the whole image processing apparatus 100. Further, in the image processing apparatus 100, the MPU 150 plays the role of, for example, the below-described processing unit 110.

The ROM 152 stores control data, such as programs and calculation parameters used by the MPU 150. The RAM 154 temporarily stores programs and the like, for example, that are executed by the MPU 150.

The recording medium 156 functions as a storage unit, which stores, for example, various data such as X-ray detection data, projection data in which X-ray detection data has been converted, and applications. Here, examples of the recording medium 156 include magnetic recording media such as a hard disk, non-volatile memory such as flash memory and the like. Further, the recording medium 156 may be detachable from the image processing apparatus 100.

The input/output interface 158, for example, connects the operation input device 160 and the display device 162. The operation input device 160 functions as an operation unit (not illustrated), and the display device 162 functions as a display unit (not illustrated). Here, examples of the input/output interface 158 includes a USB terminal, a DVI (digital visual interface) terminal, a HDMI (high-definition multimedia interface) terminal, various processing circuits and the like. Further, the operation input device 160 is, for example, included on the image processing apparatus 100, and is connected with the input/output interface 158 in the image processing apparatus 100. Examples of the operation input device 160 include a button, a direction key, a rotating-type selector such as a jog dial, or a combination of these. Further, the display device 162 is, for example, included on the image processing apparatus 100, and is connected with the input/output interface 158 in the image processing apparatus 100.

Examples of the input/output interface 158 include a liquid crystal display (LCD), an organic EL display (organic electroluminescence display, also called an OLED (organic light emitting diode display)) and the like.

It is noted that the input/output interface 158 is obviously also connected to an external device, such as an operation input device (e.g., a keyboard, a mouse etc.) or a display device, as an external device of the image processing apparatus 100. Further, the display device 162 may also be a device that can perform a display and user operations.

The communication interface 164 is a communication unit included in the image processing apparatus 100, which functions as the communication unit 102 for performing wireless/wired communication with the detection apparatus 300 or an external device, such as a server, via a network (or directly). Here, examples of the communication interface 164 include a communication antenna and an RF circuit (wireless communication), an IEEE 802.15.1 port and a transmitting/receiving circuit (wireless communication), an IEEE 802.11b port and a transmitting/receiving circuit (wireless communication), or a LAN (local area network) terminal and a transmitting/receiving circuit (wired communication) and the like.

The image processing apparatus 100 performs the processing performed in the image processing method according to the present embodiment based on the configuration illustrated in FIG. 11, for example. However, the hardware configuration of the image processing apparatus 100 according to the present embodiment is not limited to the configuration illustrated in FIG. 11. For example, if the image processing apparatus 100 performs the processing as a standalone configuration, the image processing apparatus 100 may be configured without the communication device 164. In addition, the image processing apparatus 100 may also be configured without the operation input device 160 or the display device 162.

An example of the configuration of the image processing apparatus 100 will be described again with reference to FIG. 10. The communication unit 102 is a communication unit included in the image processing apparatus 100, which performs wireless/wired communication with the detection apparatus 300 or an external device, such as a server, via a network (or directly). Further, communication by the communication unit 102 is controlled by the control unit 104, for example. Here, examples of the communication unit 102 include a communication antenna and an RF (radio frequency) circuit, a LAN terminal, a transmitting/receiving circuit and the like. However, the configuration of the communication unit 102 is not limited to these examples. For example, the communication unit 102 may have a configuration that supports an arbitrary standard that is capable of performing communication, such as a USB terminal and a transmitting/receiving circuit, or an arbitrary configuration that is capable of communicating with an external device via a network.

The control unit 104 is configured from a MPU, for example, which plays the role of controlling the whole image processing apparatus 100. Further, the control unit 104 which includes, for example, the processing unit 110, plays the lead role in the processing performed in the image processing method according to the present embodiment.

The processing unit 110, which plays the lead role in the processing performed in the image processing method according to the present embodiment, forms an X-ray image based on X-ray detection data by processing projection data in which parallel X-ray detection data (X-ray detection data representing a detection result of parallel beam X-rays output from an X-ray source) has been converted by projection. More specifically, the processing unit 110 forms an X-ray image based on X-ray detection data by performing the processing according to the above-described first example, the processing according to the above-described second example, or the processing according to the above-described third example.

Here, for example, if it is possible to directly process the projection data in which parallel X-ray detection data has been converted, such as when the communication unit 102 has received projection data in which parallel X-ray detection data has been converted, the processing unit 110 process that projection data. Further, for example, in the case of processing the parallel X-ray detection data, such as when the communication unit 102 has received parallel X-ray detection data, the processing unit 110 converts the parallel X-ray detection data and processes the converted projection data. It is noted that the processing unit 110 can also process parallel X-ray detection data stored in a storage unit (described below) or the like, or projection data stored in the storage unit (described below) or the like in which parallel X-ray detection data has been converted.

The control unit 104 plays the lead role in the processing performed in the image processing method according to the present embodiment due to its inclusion of the processing unit 110, for example.

The image processing apparatus 100 performs the processing performed in the image processing method according to the present embodiment based on the configuration illustrated in FIG. 10, for example.

Therefore, the image processing apparatus 100 can achieve a higher quality X-ray image while reducing the calculation costs for forming an X-ray image even further. Further, the image processing apparatus 100 achieves the effects gained from performing the processing according to the above-described first example when performing the processing according to the above-described first example, achieves the effects gained from performing the processing according to the above-described second example when performing the processing according to the above-described second example, and achieves the effects gained from performing the processing according to the above-described third example when performing the processing according to the above-described third example.

It is noted that the configuration of the image processing apparatus according to the present embodiment is not limited to the configuration illustrated in FIG. 10.

(i) First Modified Example

For example, the image processing apparatus according to the present embodiment may further include a detection unit (not illustrated) having a similar function and configuration to the detection apparatus 300 illustrated in FIG. 9. The detection unit (not illustrated) detects parallel beam X-rays and generates parallel X-ray detection data, for example. Further, the detection unit (not illustrated) may also have a function for, for example, detecting parallel beam X-rays, generating parallel X-ray detection data, and converting the generated parallel X-ray detection data into projection data by projection.

When the detection unit (not illustrated) detects parallel beam X-rays and generates parallel X-ray detection data, for example, the processing unit 110 converts the X-ray detection data generated by the detection unit (not illustrated) into projection data by projection, and processes the converted projection data. Further, in the case of the detection unit (not illustrated) detecting parallel beam X-rays, generating parallel X-ray detection data, and converting the generated parallel X-ray detection data into projection data by projection, the processing unit 110 processes the projection data converted by the detection unit (not illustrated). It is noted that the processing unit 110 according to the first modified example of the present embodiment may also process parallel X-ray detection data stored in a storage unit (described below), or projection data in which parallel X-ray detection data stored in a storage unit (described below) has been converted.

Similar to the image processing apparatus 100 illustrated in FIG. 10, even if it further includes a detection unit (not illustrated), the image processing apparatus according to the first modified example of the present embodiment can perform the processing performed in the image processing method according to the present embodiment. Therefore, the image processing apparatus according to the first modified example of the present embodiment can obtain the same effects as the image processing apparatus 100 illustrated in FIG. 10.

The image processing apparatus according to the present embodiment may further include, in addition to the configuration of the image processing apparatus according to the first modified example of the present embodiment, an X-ray output unit (not illustrated) having a similar function and configuration to the X-ray output apparatus 200 illustrated in FIG. 9. The X-ray output unit (not illustrated) has an X-ray source that outputs parallel beam X-rays, for example. Further, the generation of the X-rays in the X-ray output unit (not illustrated) is controlled by the control unit 104, for example.

With the image processing apparatus according to the second modified example of the present embodiment, which in addition to the configuration illustrated in FIG. 10, further includes an X-ray output unit (not illustrated) and a detection unit (not illustrated), the detection unit (not illustrated) can detect parallel beam X-rays output from the X-ray output unit (not illustrated), for example, and the processing unit 110 can process projection data in which parallel X-ray detection data representing a detection result has been converted by the detection unit (not illustrated). It is noted that the processing unit 110 according to the second modified example of the present embodiment can also process parallel X-ray detection data stored in a storage unit (described below) or the like, or projection data stored in the storage unit (described below) or the like in which parallel X-ray detection data has been converted.

Therefore, even with a configuration that additionally includes an X-ray output unit (not illustrated) and a detection unit (not illustrated), similar to the image processing apparatus 100 illustrated in FIG. 10, the image processing apparatus according to the second modified example of the present embodiment can perform the processing performed in the image processing method according to the present embodiment. Therefore, the image processing apparatus according to the first modified example of the present embodiment can obtain the same effects as the image processing apparatus 100 illustrated in FIG. 10.

(iii) Third Modified Example

When the image processing apparatus according to the present embodiment performs processing as a standalone configuration, for example, the image processing apparatus according to the present embodiment may be configured without the communication unit 102.

Although an image processing apparatus was described above as an embodiment of the present disclosure, the present embodiment is not limited to this example. The present embodiment can also be used in various devices that are capable of processing an image, such as a computer like a PC (personal computer) or a server, a CT apparatus (an apparatus that uses 360° direction projection data), an apparatus having a tomosynthesis function (an apparatus that uses projection data of a controlled angle direction, such as 180° direction projection data), a communications device such as a smartphone and the like. Further, the present embodiment can also be applied in a processing IC (integrated circuit) that can be incorporated in such devices.

(Program According to the Present Embodiment)

By executing on a computer a program that makes a computer function as the image processing apparatus according to the present embodiment (e.g., a program capable of executing the processing performed in the image processing method according to the present embodiment, such as a program that makes a computer function as the processing unit 110 illustrated in FIG. 10), a higher quality X-ray image can be achieved while reducing the calculation costs for forming an X-ray image even further.

It should be understood by those skilled in the art that various modifications, combinations, sub-combinations and alterations may occur depending on design requirements and other factors insofar as they are within the scope of the appended claims or the equivalents thereof.

For example, although a program (computer program) that makes a computer function as the image processing apparatus according to the present embodiment was described above, the present embodiment can further provide a recording medium in which this program is stored.

The above-described configuration illustrates one example of the present embodiment, and naturally comes under the technical scope of an embodiment according to the present disclosure.

Additionally, the present technology may also be configured as below.

(1) An image processing apparatus including:
a processing unit configured to processes projection data in which X-ray detection data representing a detection result of parallel beam X-rays output from an X-ray source has been converted by projection, and form an X-ray image based on the X-ray detection data.

(2) The image processing apparatus according to (1), wherein the processing unit is configured to divide the projection data and form the X-ray image per piece of divided projection data.

(3) The image processing apparatus according to (1), wherein the processing unit is configured to form the X-ray image each time the projection data is acquired.

(4) The image processing apparatus according to any one of (1) to (3), further including:
a detection unit configured to detect the parallel beam X-rays, generate the X-ray detection data, and convert the generated X-ray detection data into the projection data,
wherein the processing unit is configured to process the projection data converted by the detection unit.

(5) The image processing apparatus according to any one of (1) to (3), further including:
a detection unit configured to detect the parallel beam X-rays and generate the X-ray detection data,
wherein the processing unit is configured to convert the X-ray detection data generated by the detection unit into the projection data, and process the converted projection data.

(6) The image processing apparatus according to (4) or (5), further including:
an X-ray output unit that includes the X-ray source for outputting the parallel beam X-rays.

(7) An image processing method including:
processing projection data in which X-ray detection data representing a detection result of parallel beam X-rays output from an X-ray source has been converted by projection, and forming an X-ray image based on the X-ray detection data.

(8) An image processing system including:
an X-ray output apparatus that includes an X-ray source for outputting parallel beam X-rays;
a detection apparatus configured to detect the parallel beam X-rays, generate X-ray detection data representing a detection result of the parallel beam X-rays, and convert the generated X-ray detection data into projection data by projection; and
an image processing apparatus that includes a processing unit configured to process projection data in which the X-ray detection data has been converted, and form an X-ray image based on the X-ray detection data.

The present disclosure contains subject matter related to that disclosed in Japanese Priority Patent Application JP 2012-185292 filed in the Japan Patent Office on Aug. 24, 2012, the entire content of which is hereby incorporated by reference.

What is claimed is:

1. An image processing apparatus comprising:
a processing unit configured to process projection data in which X-ray detection data representing a detection result of parallel beam X-rays output from an X-ray source through a layer of a target has been converted by projection and form an X-ray image from the projection data corresponding to the layer.

2. The image processing apparatus according to claim 1, wherein the processing unit is configured to divide the projection data and form the X-ray image per piece of divided projection data.

3. The image processing apparatus according to claim 1, wherein the processing unit is configured to form the X-ray image each time the projection data is acquired.

4. The image processing apparatus according to claim 1, further comprising:
a detection unit configured to detect the parallel beam X-rays, generate the X-ray detection data, and convert the generated X-ray detection data into the projection data by projection,
wherein the processing unit is configured to process the projection data converted by the detection unit.

5. The image processing apparatus according to claim 4, further comprising:
an X-ray output unit that includes the X-ray source for outputting the parallel beam X-rays.

6. The image processing apparatus according to claim 1, further comprising:
a detection unit configured to detect the parallel beam X-rays and generate the X-ray detection data,
wherein the processing unit is configured to convert the X-ray detection data generated by the detection unit into the projection data, and process the converted projection data.

7. An image processing method comprising:
processing projection data in which X-ray detection data representing a detection result of parallel beam X-rays output from an X-ray source through a layer of a target has been converted by projection and forming an X-ray image from the projection data corresponding to the layer.

8. An image processing system comprising:
an X-ray output apparatus that includes an X-ray source for outputting parallel beam X-rays;
a detection apparatus configured to detect the parallel beam X-rays, generate X-ray detection data representing a detection result of the parallel beam X-rays through a layer of a target, and convert the generated X-ray detection data corresponding to the layer into projection data by projection; and an image processing apparatus that includes a processing unit configured to process the projection data and form an X-ray image from the projection data corresponding to the layer.

* * * * *